US00PP34197P2

(12) United States Plant Patent
Hansen

(10) Patent No.: US PP34,197 P2
(45) Date of Patent: May 3, 2022

(54) ***LEUCANTHEMUM* PLANT NAMED 'SPUN SILK'**

(50) Latin Name: ***Leucanthemum* x *superbum***
Varietal Denomination: Spun Silk

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,594

(22) Filed: Aug. 30, 2021

(51) Int. Cl.
*A01H 5/02* (2018.01)
*A01H 6/14* (2018.01)

(52) U.S. Cl.
USPC ..... Plt./285
CPC ..... *A01H 6/14* (2018.05)

(58) Field of Classification Search
USPC ..... Plt./285
CPC ..... A01H 6/14
See application file for complete search history.

*Primary Examiner* — Anne Marie Grunberg

(57) ABSTRACT

The new Shasta daisy plant, *Leucanthemum* 'Spun Silk', is a sturdy plant with dark-green serrated foliage and stiff stems. The numerous freely-flowering inflorescences producing buds beginning with pale cream ray florets developing to near white. The outer ray florets are lanceolate to linear and deeply emarginate and the center disk florets are yellow. Flowering repeats into fall if deadheaded. The new plant is useful in the landscape as a long-flowering border, in mass, as accent plants and containerized for patio or indoor use, or as a cut flower.

1 Drawing Sheet

Botanical classification: *Leucanthemum* x *superbum* (Bergmans ex J.W.Ingram) D.H.Kent.

Variety denomination: 'Spun Silk'.

STATEMENT REGARDING PRIOR DISCLOSURES UNDER 37 CFR 1.77(B)(6)

The first non-enabling disclosure of the claimed plant was made by Walters Gardens, Inc. on Dec. 1, 2020 in the form of a website brief description and photograph followed by a short description and photograph in the "Walters Gardens 2021-2022 Catalog" by Walters Gardens, Inc first distributed on May 21, 2021. The first enabling disclosure of a sales of the claimed plant was on Aug. 31, 2020 by Walters Gardens, Inc. Walters Gardens, Inc. obtained the new plant and information about the new plant directly from the inventor. No plants of *Leucanthemum* 'Spun Silk' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The original *Leucanthemum* x *superbum*, or Shasta daisies, were bred by Luther Burbank in the late 1800's as a cross between *Leucanthemum maximum* (Ramond) DC. with *Leucanthemum lacustre* (Broth.) Samp. and *Leucanthemum nipponicum*. The new plant, *Leucanthemum* 'Spun Silk' originated from a planned breeding program of the inventor at a wholesale perennial nursery in Zeeland, Mich., USA. The new *Leucanthemum* was a single plant selected from a group of seedlings from a cross on Jul. 30, 2015 between the proprietary, unnamed, unreleased hybrid known only as 13-129 (not patented) and the proprietary, unnamed, unreleased hybrid known only as 11-3 (not patented). The individual plant that eventually became 'Spun Silk' was first evaluated in the summer of 2016 and originally given the breeder number 15-115-30 through the subsequent evaluations.

The present invention relates to a new and distinct cultivar of Shasta daisy botanically known as *Leucanthemum* x *superbum* and hereinafter referred to by the cultivar name 'Spun Silk' or the new plant.

Asexual reproduction of the new cultivar by basal cuttings and shoot tip tissue culture at the same nursery in Zeeland, Mich. as early as the summer of 2017 has demonstrated that the new cultivar reproduces true to type with all of the characteristics of the original plant retained through successive generations of asexual propagation.

BRIEF SUMMARY OF THE INVENTION

The new plant, *Leucanthemum* 'Spun Silk', is most closely compared to 'Aglaia' (not patented) 'Sante' U.S. Plant Pat. No. 19,829, 'Marshmallow' U.S. Plant Pat. No. 33,878, 'Cream Puff' U.S. Plant Pat. No. 30,074, 'Whoops-a-Daisy' U.S. Plant Pat. No. 27,259, 'Laspider' (not patented) and 'Old Court' (not patented).

In test trials in Zeeland, Mich., 'Aglaia' has a taller and more open in habit and has flowers that have multiple rows of ray florets. 'Sante' is smaller in habit and the ray floret ligules are more numerous and have a more yellowish coloration. 'Marshmallow' has a slightly smaller habit with inflorescences that have multiple rows of ray florets. 'Cream Puff' has a shorter habit with ray florets that are more yellow. 'Whoops-a-Daisy' has a shorter dome-shaped habit in flower and the ray florets are not as deeply emarginate. 'Laspider' has a much shorter and compact habit and has more ray florets per inflorescence. 'Old Court' has a taller habit with less branching, fewer ray florets per inflorescence and the ray floret ligules are narrower and more arching.

The female parent is not as heavily branched and the ray florets are wider. The male parent has ray florets that are wider and more creamy-yellow colored, higher flower number per plant and is more compact in habit.

*Leucanthemum* 'Spun Silk' differs from all cultivars known to the inventor in the following combined traits:

1. Sturdy, dense, mounded plants with dark-green serrated foliage and stiff stems;
2. Inflorescence of numerous capitulum.
3. The double row of ray florets with narrow lanceolate to linear ligules that are deeply emarginate;
4. Center disk florets of yellow;
5. Ray floret ligules beginning pale cream and lightening to near white;
6. Freely flowering habit and repeating if deadheaded.

BRIEF DESCRIPTION OF THE PHOTOGRAPHS

The photographs of 'Spun Silk' demonstrate the overall appearance and landscape qualities of the new plant, including the unique traits planted in a full-sun trial garden in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
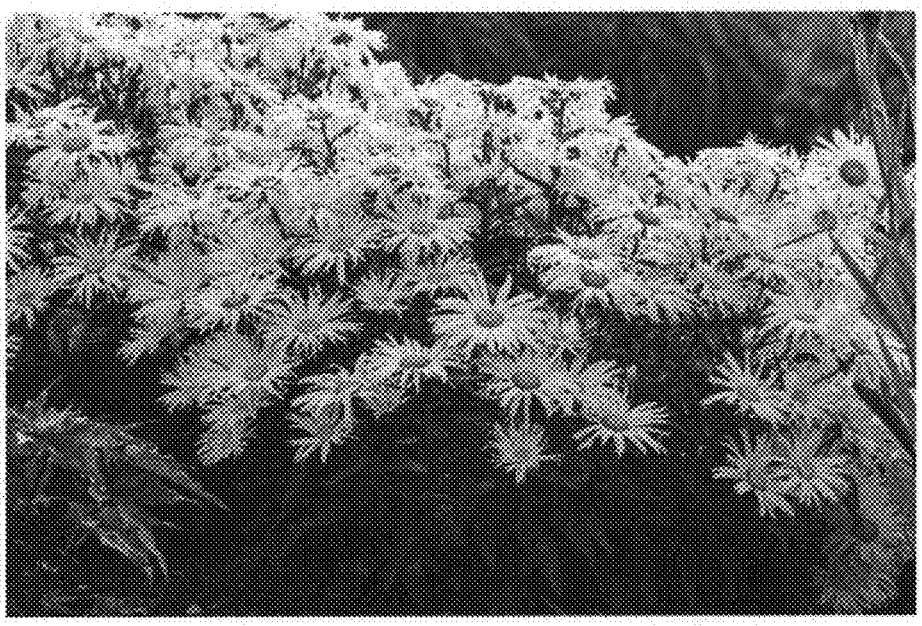
FIG. 1 shows a two-year-old new plant at peak flowering with inflorescences covering the top of the plant.
Figure 2:
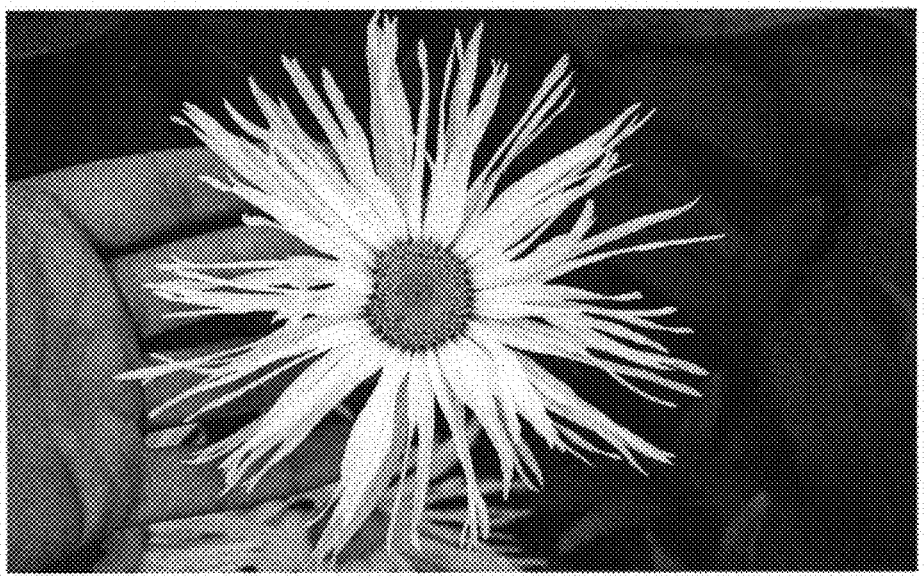
FIG. 2 shows a close-up of the inflorescence from above.

The following descriptions and color references are based on the 2015 edition of The Royal Horticultural Society Colour Chart except where common dictionary terms are used. The new plant has not been observed in all possible environments and conditions. The phenotype of *Leucanthemum* 'Spun Silk' may vary with different growing conditions such as changes in temperature, light intensity, water availability, fertility, but without change in the genotype.

The plants used for description purposes were two-year-old and were grown in Zeeland, Mich. in a full-sun, loamy-sand trial plot environment with supplemental water and limited fertilizer as needed. Summer temperatures range from night lows of about 10° C. to daytime highs of about 34° C. Measurements and numerical values represent averages of trial plants.

Botanical classification: *Leucanthemum* x *superbum;*

Parentage: Female parent is the proprietary hybrid 13-129, male parent is the proprietary hybrid 11-3;

Habit: Herbaceous perennial with about 23 branched stems arising from rhizome base; each stem having three to eight inflorescences each, rarely two; about 48 cm tall and 71 cm across with rounded top;

Roots: Fibrous, thin, heavily branched; root color nearest RHS 158D depending on soil type;

Propagation: Tip cuttings or tissue culture; about two weeks to produce roots from cutting; about 33 weeks to finish to flower in 3.8 liter pot depending on season;

Stems: About 23 main stems per plant; strong; mostly upright; canaliculated; sparsely puberulent to hispidulous; terete, hollow in distal portion; 9.0 mm diameter at base; to 38 cm long; about 13 nodes before terminal inflorescence; average internode length about 1.0 cm;

Stem color: Nearest RHS 137B in channels and ribs nearest RHS 137A;

Axillary branches: Three to eight; between 6.0 to 27.0 cm long and 4.0 to 6.0 mm diameter; at angles of about 30° from main stem; side flowers rising above initial flower;

Axillary branch color: Nearest RHS 137B in channels and ribs nearest RHS 137A;

Leaves: Lanceolate to spatulate; apex acute; base attenuate; alternate; sparsely puberulent adaxial and abaxial; margin serrate and ciliolate with up to about fifteen teeth per side, and size to about 4.0 mm long and 3.0 mm wide; adaxial and abaxial nearly microscopically puberulent; stiff and thick; lowest leaves about 17.5 cm long and 3.8 cm wide, average about 14.0 cm long and 3.0 cm wide; no fragrance detected;

Leaf color: Young adaxial between RHS 146B and RHS 144A, abaxial between RHS 146C and RHS 146C; mature adaxial nearest RHS NN137A, abaxial nearest RHS 137A;

Veins: Anastomosing; glabrescent adaxial and abaxial; adaxial slightly raised, abaxial midrib costate and secondary veins smooth;

Vein color: Adaxial midrib nearest RHS 146B, secondary veins nearest RHS NN137A; abaxial midrib nearest RHS 144A and secondary veins nearest RHS 144A;

Inflorescence: Capitate, about 30 per plant at one time; primary inflorescence 13.0 cm across and 3.0 cm tall; comprising two outer rows of larger ray florets, and central disk florets; individual inflorescence lasting about three weeks on or cut from plant; upright;

Fragrance: Slight dirty fragrance detected;

Flowering period: Early summer (late June) to early autumn in Michigan if deadheaded;

Peduncle: Strong, stiff; sparsely hispidulous to puberulent; cylindrical; longitudinally fluted; 8.0 to 19.0 cm long and about 3.5 mm diameter at base; upwardly;

Peduncle color: Nearest RHS 137B in channels and ribs nearest RHS 137A;

Bud: With ray florets still vertical-cylindrical, 15.0 mm across ray florets and 32.0 mm from base of phyllaries to apex of capitulum;

Bud color: Adaxial and abaxial ray floret ligule coloration nearest RHS 155B; phyllaries nearest RHS 137A in center and margin nearest RHS 144A;

Ray florets: Two rows on the exterior; about 40 per inflorescence; lanceolate to linear; emarginate cleft to about 32.0 mm deep, average about 20.0 mm deep with other notch cut an average of 5.0 mm deep; base attenuate; margin entire; glabrous adaxial and abaxial;

Ray ligule size: To about 53.0 mm long and 10.0 mm wide, average about 50.0 mm long and 8.5 mm wide;

Disk florets: To about 500 to 700 per inflorescence, inflorescences disk variable, to about 35.0 mm across and about 15.0 mm tall; individual floret about 7.5 mm tall and 3.5 mm wide, five tepals, about 6.0 mm long; with acute apex, fused in basal 5.0 mm;

Ray floret color: As ligules are first expanding adaxial and abaxial between RHS NN155A and RHS NN155B with base nearest RHS 146C; mature ligule adaxial and abaxial nearest RHS NN155B with base nearest RHS 146C;

Disk floret color: Mature adaxial and abaxial tepals nearest RHS 14A distally and basal 3.0 mm nearest RHS 146B, young tepals adaxial and abaxial nearest RHS 14A distally and basal 3.0 mm nearest RHS 146B;

Androecium: Five stamens connate around style;

*Anther*.—Five; connate into tube; about 3.0 mm long and less than one mm diameter, not present in ray florets, functional in disk florets; coloration nearest RHS 21A.

*Filaments*.—Fused together at apex, 2.0 mm to 3.0 mm long and less than 0.2 mm diameter, filament coloration translucent to nearest RHS 155C.

*Pollen*.—Only found in disk florets; color nearest RHS 21A.

Gynoecium: In ray florets and disk florets; to about 9.0 mm long;

*Style*.—About 5.0 mm long and less than 0.5 mm diameter, split and curved at apical 1.0 mm; color nearest RHS 145C.

*Stigma*.—To about 1.5 mm long and less than 0.5 mm diameter; color nearest RHS 9C.

*Ovary*.—To about 3.0 mm long and 1.0 mm diameter; color nearest RHS 146D.

Involucre: Made of about three layers of phyllaries; to 30.0 mm across and 7.0 mm tall;

Phyllaries: Lanceolate; glabrous; margin entire and transparent; apex acute; base truncate; to about 68 per head arranged in about three imbricate rows; 8.0 mm long and 4.0 mm wide;

Phyllaries color: Adaxial center lustrous, nearest RHS 137B, margin transparent, region between margin and center nearest RHS N199B; abaxial center between RHS 138A and RHS 146B, margin transparent, region between center and margin nearest RHS N199B;

Fruit: Achene, pointed at base and rounded at distal end with longitudinal color striations nearest RHS N200A and lighter than RHS 155D; about 3 to 4 mm long and 1.5 mm across;

*Leucanthemum* 'Spun Silk' grows best with adequate moisture but can tolerate some dryness once established. Vernalization is not required for flowering but is beneficial. The new plant is tolerant of high temperatures of at least 36° and cold hardy to at least USDA zone 5 as well as able to tolerate strong wind and rain. Other disease or pest resistance beyond that common to Shasta daisy has not been observed.

I claim:

1. The new and distinct Shasta daisy *Leucanthemum* plant named 'Spun Silk' as herein shown and described.

* * * * *